(12) United States Patent
Burgos et al.

(10) Patent No.: US 7,586,015 B2
(45) Date of Patent: Sep. 8, 2009

(54) PROCESS FOR THE PREPARATION OF 1,3,2-OXAZABOROLIDINE COMPOUNDS

(75) Inventors: Alain Burgos, Les Ponts-de-Ce (FR); Stëphane Frein, Saint-Aubin-de-Luigné (FR)

(73) Assignee: Zach System, Avrille (FR)

( * ) Notice: Subject to any disclaimer, the term of this patent is extended or adjusted under 35 U.S.C. 154(b) by 0 days.

(21) Appl. No.: 11/698,710

(22) Filed: Jan. 25, 2007

(65) Prior Publication Data

US 2008/0139851 A1 Jun. 12, 2008

(30) Foreign Application Priority Data

Dec. 12, 2006 (FR) .................................. 06 55449

(51) Int. Cl.
C07C 33/34 (2006.01)
C07C 33/36 (2006.01)
C07C 33/38 (2006.01)

(52) U.S. Cl. ........................ 568/807; 568/808; 568/881; 568/6; 544/229; 546/13; 546/344; 548/110; 549/213

(58) Field of Classification Search ................ 568/807, 568/808, 881, 6; 544/229; 546/13, 344; 548/110; 549/213
See application file for complete search history.

(56) References Cited

U.S. PATENT DOCUMENTS

| 6,025,531 A | * | 2/2000 | Yoneyoshi et al. .......... 568/807 |
| 6,509,472 B2 | * | 1/2003 | Draper ....................... 548/110 |
| 2008/0200728 A1 | * | 8/2008 | Burkhardt et al. ............... 568/6 |

FOREIGN PATENT DOCUMENTS

| EP | 0 305 180 | | 8/1988 |
| WO | WO 2006/134074 | * | 12/2006 |

OTHER PUBLICATIONS

Jabbour et al., Synthesis and Evaluation of Oxazaborolidines for Antibacterial Activity against Streptococcus mutans, Journal of Medicinal Chemistry (2004), 47(10), 2409-2410.*
Gilmore et al., Synthetic Applicability and in Situ Recycling of a B-Methoxy Oxazaborolidine Catalyst Derived from cis-1-Amino-indan-2-ol, Org. Lett., 6 (16), 2805-2808, 2004.*
Barker et al., {Kinetic resolution of racemic pyrrolidine-2,5-diones using chiral oxazaborolidine catalysts, Chem. Commun., 2008, 2218 — 2220}.*
International Search Report mailed Jul. 25, 2007.
Corey et al., 1992, *Tetrahedron Letters*, 33 (29): 4141-4144, "A New Process for the Generation of 1,3,2-oxazaborolidines, Catalysts for Enantioselective Synthesis."
Corey et al., 1998, *Angw. Chem. Int. Ed.*, 37:1986-2012, "Reduction of Carbonyl Compounds with Chiral Oxazaborolidine Catalysts: A New Paradigm for Enantioselective Catalysis and a Powerful New Synthetic Method."
Glushkov et al., 2004, *Russian Chemical Reviews*, 73 (6) 581-608, "Chiral 1,3,2-oxazaborolidines in asymmetric synethesis: recent advances."
International Search Report for PCT/FR2007/052488, mailed Sep. 4, 2008.
Written Opinion for PCT/FR2007/052488.
Form PCT/ISA/220 for PCT/FR2007/052488.
Gilmore et al., "Synthetic applicability and *in Situ* recycling of a B-Methoxy Oxazaborolidine catalyst derived from *cis*-1-Amino-indan-2-ol," *Org. Lett.* (2004) 6 (16): 2805-2808.
Brown et al., "Organoboranes. 39. Convenient procedures for the preparation of methylboronic acid and trimethylboroxin," *Organometallics* (1985) 4: 816-821.
International Search Report for PCT/FR2007/052488, mailed Sep. 4, 2008.
Written Opinion for PCT/FR2007/052488. Oct. 4, 2008.
Form PCT/ISA/220 for PCT/FR2007/052488. Oct. 4, 2008.

* cited by examiner

*Primary Examiner*—Sikarl A Witherspoon
*Assistant Examiner*—Chukwuma O Nwaonicha
(74) *Attorney, Agent, or Firm*—Merchant & Gould P.C.

(57) ABSTRACT

A process is used for the preparation of 1,3,2-oxazaborolidine compounds.

This process prepares compounds of formula (I) or (IA):

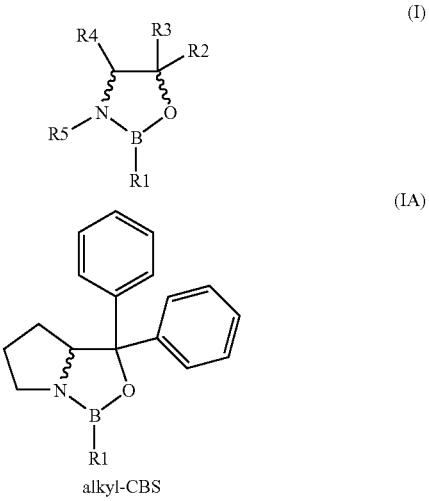

alkyl-CBS in which:
R1 is an alkyl or an aryl; and
R2, R3, R4 and R5 are especially a hydrogen atom or an alkyl, wherein the following are reacted in two steps:
a) a boric precursor compound with an acetal compound to give a boronate compound; and
b) the boronate compound with an amino alcohol compound.

This process avoids by-products and exhibits a very good stereospecificity.

24 Claims, No Drawings

PROCESS FOR THE PREPARATION OF 1,3,2-OXAZABOROLIDINE COMPOUNDS

The present invention relates to a novel process for the preparation of the compounds of formula (I), which are called CBS compounds. More particularly, the invention relates to a process for the preparation of an optically active alkyl-CBS compound, specifically Me-CBS, of formula (IA).

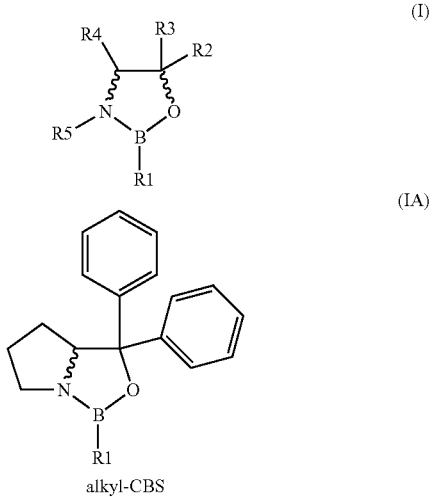

alkyl-CBS

The compounds of formulae (I) and (IA) are precursors for the synthesis of catalysts that are very widely used in processes for the enantioselective reduction of a prochiral ketone.

PRIOR ART

The literature discloses processes for the synthesis of the compounds of formula (I), and particularly the compounds of formula (IA), by reacting a chiral amino alcohol in the presence of either a boroxine ($R1_3B_3O_3$) or a boronic acid ($R1B(OH)_2$) or an alkylboronate ($R1B(OR')_2$). These processes, which are industrialized, lead to the formation of a by-product, such as water, and contamination with boronic acid.

In all cases the water has to be removed from the medium by carrying out several azeotropic distillations.

It is in fact known that the presence of water or contamination of the compounds of formula (I) with boronic acid reduces the performance of the stereospecific activity of the catalysts obtained from said compounds.

More specifically, the literature describes the preparation of the compound of formula (IA) in which R1 is methyl, namely optically active Me-CBS, from optically active diphenylprolinol in the presence of either trimethylboroxine ($B_3Me_3O_3$) or methylboronic acid ($MeB(OH)_2$) or bis(2,2,2-trifluoroethyl) alkyl-boronate.

From a Boroxine or a Boronic Acid

The article Russian Chemical Reviews 2004, 73(6), pp 581-608, by the authors Glushkov V. and Tolstikov A., describes processes for the preparation of the compounds of formula (I) or (IA) from a boroxine or a boronic acid and the impact of the by-products formed when optically active Me-CBS is used in reactions for the enantioselective reduction of a prochiral ketone.

The article Angew. Chem. Int. Ed. 1998, 37(29), p. 1989, by the authors Corey E. and Helal C., mentions the preparation of a compound of formula (IA), namely optically active Me-CBS, from optically active diphenylprolinol in the presence of methylboronic acid (MeB(OH)$_2$) using toluene as solvent and removing the water formed by azeotropic distillation.

From Boronates

The article Tetrahedron Letters 1992, 33(29), pp 4141-4144, by the authors Corey E. and Link J., describes the preparation of the compound of formula (IA) in which R1 is ethyl, namely optically active Et-CBS, from optically active diphenylprolinol in the presence of bis(2,2,2-trifluoroethyl) ethylboronate ($CH_3CH_2B(OCH_2CF_3)_2$). The use of bis(2,2,2-trifluoroethyl) ethylboronate as starting material remains a laboratory process because its preparation requires a 2-step process, as mentioned in said article.

The article Organic Letters 2004, 6(16), pp 2805-2808, by the authors Muldowney M. et al., describes the preparation of the compounds of formula (I) from cis-1-aminoindan-2-ol and methyl diisopropylborate. This process is limited in the preparation of the methyl diisopropylborate, as described in the articles Organometallics, 1983, 2, pp 1316-1319 and Organometallics, 1985, 4, pp 816-821, by the authors H. C. Brown and T. E. Cole.

Thus the processes for the preparation of the compounds of formula (I) described in the literature remain industrially imperfect because of the formation of water or contamination with boronic acid. The latter compounds have to be removed in order to ensure a high quality of the products of formula (I) or (IA), which is demanded for their use as a precatalyst in reactions for the enantioselective reduction of a prochiral ketone.

OBJECTS OF THE INVENTION

One main object of the present invention is to provide a process for the preparation of the compounds of formula (I), referred to as CBS compounds, and particularly a process for the preparation of an optically active alkyl-CBS compound, specifically methyl-CBS or ethyl-CBS, of formula (IA) given above, in which the step for the elimination of water by azeotropic distillation is unnecessary or omitted.

Another main object of the present invention is to provide a novel process for the preparation of the above-mentioned compounds of formula (I) or (IA) which completely avoids the formation of water or does not form a substantial amount of water, or does not produce any contamination or substantial contamination with boronic acid.

Another main object of the present invention is to provide a process for the preparation of the compounds of formula (I) or (IA) which is of very great economic value because it uses either less starting material, such as a boroxine, or an inexpensive starting material, such as a boronic acid.

Another main object of the present invention is to solve these technical problems by means of a process which affords a high purity of the above-mentioned products of formula (I) or (IA) so as to allow their use as precatalysts in reactions for the enantioselective reduction of a prochiral ketone.

Another main object of the present invention is to provide a novel process for the preparation of the above-mentioned compounds of formula (I) or (IA) with a high yield and in quantities compatible with a preferably industrial-scale production of pharmaceutical grade.

Thus the present invention solves the above-stated technical problems for the first time by developing a process for the preparation of the compounds of formula (I) or (IA) which completely or essentially avoids the formation of water or contamination with a boronic acid (R1B(OH)$_2$).

Said boronic acid is known to decrease the enantiomeric excess obtained when the compounds of formula (I) or (IA) are used as precatalysts in reactions for the enantioselective reduction of a prochiral ketone.

The present invention therefore makes it possible to obtain the compounds of formula (I), and more specifically the compounds of formula (IA), chemically pure and at a very advantageous financial cost for industrial use.

DETAILED DESCRIPTION OF THE INVENTION

According to a first feature, the Applicant has developed a process for the preparation of the compounds of formula (I) or (IA):

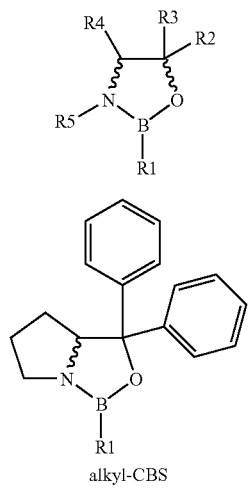

in which:

R1 is an alkyl or an aryl;

R2, R3, R4 and R5 independently are a hydrogen atom, an alkyl or an aryl, it being possible for the alkyl or aryl groups to have one or more hydrogen atoms replaced by one or more substituents;

R4 and R5 together form a heterocycle with the nitrogen atom, which itself comprises one or more substituents; and R4 and R3 together form a carbocycle, which itself comprises one or more substituents, wherein the following are reacted, preferably in situ, in two steps:

a) a boric precursor compound with a compound of formula (III) to give a boronate compound of formula (IV) according to the chemical reaction below:

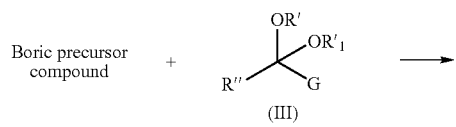

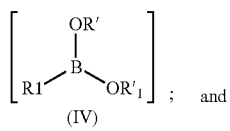

b) the boronate compound of formula (IV) with an amino alcohol compound of formula (V) according to the chemical reaction below:

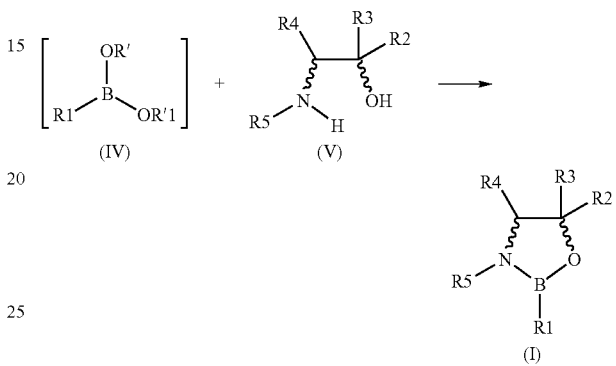

in which:

G is an alkoxy group (OR'2) or an amino group (NR'R'1);

R' and R'1 are identical or different and are an alkyl group or an acyl;

R' and R'1 can together form a C$_{2-3}$ carbocycle optionally substituted by an alkyl;

R" is a hydrogen atom, an alkyl group or an aryl group; and

R1, R2, R3, R4 and R5 are as defined above, to give the above-mentioned compound of formula (I), specifically of formula (IA).

In a first advantageous embodiment of the invention, the process according to the invention comprises obtaining the boronate compound of formula (IV) by reacting the boric precursor compound consisting of a boroxine of formula (II) with an acetal of formula (III) according to the chemical reaction below:

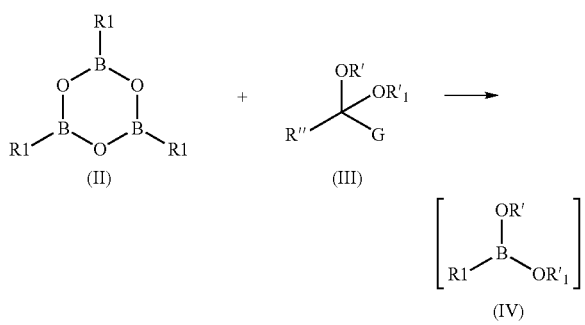

in which:

G is an alkoxy group (OR'2) or an amino group (NR'R'1);

R', R'1 and R'2 are identical or different and are an alkyl group or an acyl;

R' and R'1 together form a C$_{2-3}$ carbocycle optionally substituted by an alkyl; and R" is a hydrogen atom, an alkyl group or an aryl group.

In another advantageous embodiment of the invention, the process comprises preparing the boronate compound of formula (IV) from the boric precursor compound consisting of a boronic acid of formula (VI) with an acetal of formula (III) according to the chemical reaction below:

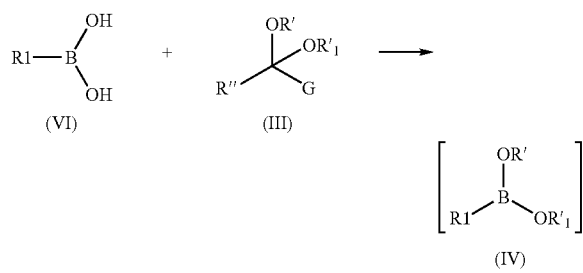

in which:
the substituents R1, R', R'1, R" and G are as defined according to the invention.

In one advantageous variant of the invention, the compound of formula (II) used in the process is a trialkylboroxine or a triarylboroxine.

In yet another variant of the invention, the compound of formula (II) used in the process is trimethylboroxine.

In another variant of the invention, the compound of formula (III) used in the process is selected from the group comprising a trialkyl or triaryl orthoformate, a formamide acetal and a trimethoxymethylaryl and/or trimethoxymethylalkyl compound.

In another particular embodiment of the invention, the compound of formula (III) in the process is trimethyl orthoformate or trimethoxymethane, dimethylformamide dimethylacetal, trimethoxymethylbenzene, 1,1,1-trimethoxyethane, 1,1,1-trimethoxypropane or 1,1,1-trimethoxy-2-methylpropane.

In yet another embodiment of the invention, the process comprises carrying out the reaction in the presence of an acid preferably selected from an organic acid, a Lewis acid and a mineral acid.

In one advantageous embodiment of the invention, the reaction takes place in the presence of an organic acid preferably comprising, essentially consisting of or consisting of methanesulfonic acid (MeSO$_3$H).

In another advantageous embodiment of the invention, the process comprises carrying out the reaction in at least one organic solvent, used by itself or in a mixture, which is selected particularly from an alcohol, a halogen compound, an aromatic compound, a nitrile compound, an ether compound and an ester compound.

In another advantageous embodiment of the invention, the process comprises carrying out the reaction in an above-mentioned organic solvent and adjusting the amount of compound of formula (III) to the amount of water present in the solvent used; in particular, the compound of formula (III) is present in an excess molar amount relative to the boric precursor compound so as to absorb the amount of water present in the solvent used and the water formed in the medium.

In one advantageous variant of the invention, the organic solvent used is toluene.

In another advantageous variant of the invention, the compound of formula (VI) in the process is an alkylboronic or arylboronic acid, particularly one that is available commercially.

In another variant of the invention, the compound of formula (VI) is methylboronic acid, particularly methylboronic acid that is available commercially.

In another advantageous variant of the invention, the amino alcohol of formula (V) in the process is a supported or unsupported, optically active compound.

In one particular variant of the invention, the amino alcohol of formula (V) is (R)- or (S)-2-(diphenylhydroxymethyl)pyrrolidine, (R)- or (S)-2-(2-dinaphthylhydroxymethyl)pyrrolidine, (1R,2S)-1-amino-2-indanol, (R)- or (S)-2-amino-3-methyl-1,1-diphenyl-1-butanol, (R)- or (S)-2-amino-3,3-dimethyl-1,1-diphenyl-1-butanol, (R)- or (S)-2-hydroxymethylindoline, (R)- or (S)-α,α-diphenyl(indolin-2-yl)methanol, (R)- or (S)-(5,5-dimethylthiazolidin-4-yl)diphenylmethanol, 2-((1R,2R,3R,5S)-2-amino-6,6-dimethylbicyclo[3.1.1]hept-3-yl)ethanol or another optically active isomer.

In another variant of the invention, the amino alcohol of formula (V) is (R)-or (S)-2-(diphenylhydroxymethyl)pyrrolidine.

In another advantageous variant of the invention, the number of mol equivalents of compound of formula (II) relative to the number of mol of amino alcohol of formula (V) is between 0.33 (II)/1 (V) and 0.37 (II)/1 (V).

In another advantageous variant of the invention, the number of mol equivalents of compound of formula (VI) relative to the number of mol of amino alcohol of formula (V) in the process is between 1 and 1.2 equivalents of (VI).

According to a second feature, the present invention also covers the use of the compound of formula (I), particularly of formula (IA), in a process for the asymmetric reduction of a prochiral ketone.

Within the framework of this use, the compound of formula (I) or (IA) can be used either without additional treatment of the medium or else after concentration of said medium.

Thus, in a first embodiment, the Applicant has developed a process for the preparation of the compounds of formula (I) wherein the compounds of formula (II) and the compounds of formula (III), and then the compounds of formula (V), are reacted in situ according to scheme S-1 below:

Scheme S-1

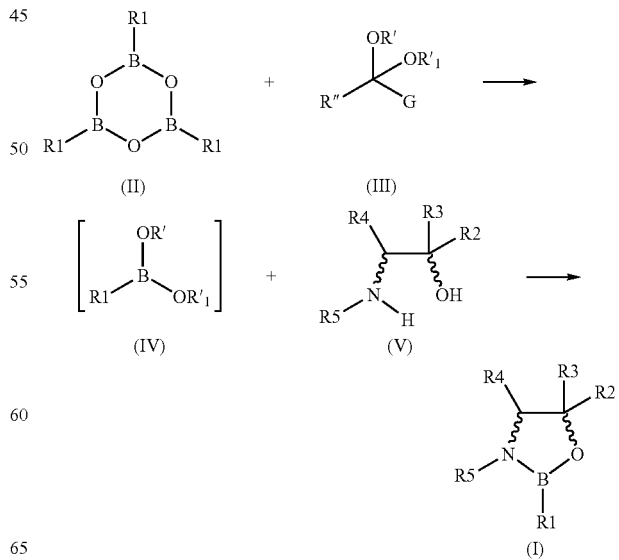

in which:

G is an alkoxy group (OR'2) or an amino group (NR'R'1);

R', R'1 and R'2 are identical or different and are an alkyl group or a carbonyl group;

R' and R'1 can together form a $C_{2-3}$ carbocycle optionally substituted by an alkyl;

R" is a hydrogen atom, an alkyl group or an aryl group;

R2, R3, R4 and R5 independently are a hydrogen atom, an alkyl or an aryl, it being possible for the alkyl or aryl groups to have one or more hydrogen atoms replaced by one or more substituents;

R4 and R5 together form a heterocycle with the nitrogen atom, which itself comprises one or more substituents; and R4 and R3 together form a $C_{3-7}$ carbocycle, which itself comprises one or more substituents.

In a second embodiment, the Applicant has developed a process for the preparation of the compounds of formula (I) wherein the compounds of formula (VI) and the compounds of formula (III), and then the compounds of formula (V), are reacted according to scheme S-2 below:

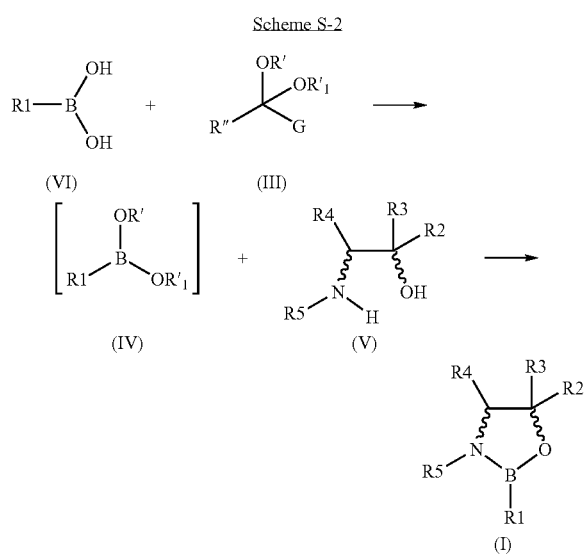

in which R1, R', R'1, R", R2, R3, R4, R5 and G are as defined above.

More precisely, in the first embodiment described by scheme S-1, the process of the invention is defined by the reaction, in an organic solvent, of a boroxine of formula (II) with an acetal of formula (III) in the presence of an acid, and by the addition of an amino alcohol of formula (V).

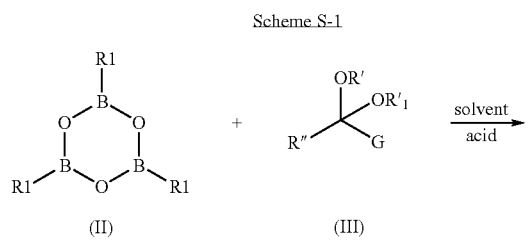

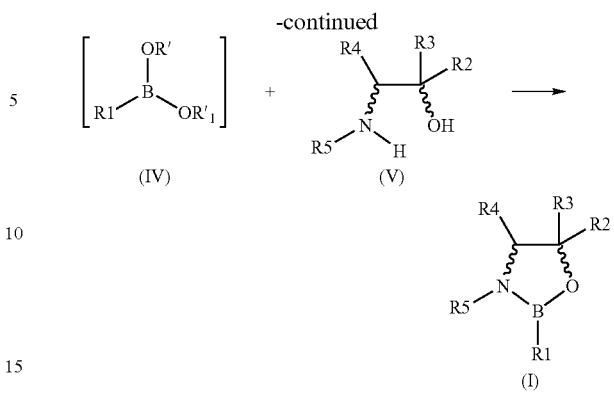

R1, R', R'1, R", R2, R3, R4, R5 and G are as defined above.

In one advantageous embodiment of the process of the invention described by scheme S-1, the compound of formula (II) used is a trialkylboroxine or a triarylboroxine. Preferably, the compound of formula (II) used is commercially available trimethylboroxine.

In one advantageous embodiment of the process of the invention described by scheme S-1, the compound of formula (III) used is a trialkyl or triaryl orthoformate, a form amide acetal or a trimethoxymethylaryl or trimethoxymethylalkyl compound. The compound of formula (III) is a commercially available compound.

The following commercially available compounds may be mentioned as examples, but without implying a limitation: trimethyl orthoformate or trimethoxymethane, triethyl orthoformate, tributyl orthoformate, N,N-dimethylformamide dimethylacetal, trimethoxymethylbenzene, 1,1,1-trimethoxyethane, 1,1,1-trimethoxypropane and 1,1,1-trimethoxy-2-methylpropane.

In one advantageous embodiment of the process of the invention described by scheme S-1, the acid used is an organic acid, a Lewis acid or a mineral acid.

By way of example, but without implying a limitation, the acid used is methanesulfonic acid ($MeSO_3H$).

In one advantageous embodiment of the process of the invention described by scheme S-1, said process is carried out in an optionally anhydrous, organic solvent, used by itself or in a mixture. Said solvent can be an alcohol, a halogen compound, an aromatic compound, a nitrile, an ether or an ester. The amount of compound of formula (III) used is adjusted to the amount of water present in the solvent.

Preferably, the solvent used is toluene.

In one advantageous embodiment of the process of the invention described by scheme S-1, the amino alcohol of formula (V) used is a supported or unsupported, optically active compound.

The following may be mentioned as examples, but without implying a limitation: (R)- or (S)-2-(diphenylhydroxymethyl)pyrrolidine, (R)- or (S)-2-(2-dinaphthylhydroxymethyl)pyrrolidine, (1R,2S)-1-amino-2-indanol, (R)- or (S)-2-amino-3-methyl-1,1-diphenyl-1-butanol, (R)- or (S)-2-amino-3,3-dimethyl-1,1-diphenyl-1-butanol, (R)- or (S)-2-hydroxymethylindoline, (R)- or (S)-α,α-diphenyl(indolin-2-yl)methanol, (R)- or (S)-(5,5-dimethylthiazolidin-4-yl) diphenylmethanol, 2-((1R,2R,3R,5S)-2-amino-6,6-dimethylbicyclo[3.1.1]hept-3-yl)ethanol or another optically active isomer, etc.

In one advantageous embodiment of the process of the invention described by scheme S-1, said process comprises carrying out the reaction at a temperature of between 5° C. and 30° C., preferably at a temperature of 20° C.

In another advantageous embodiment of the process of the invention described by scheme S-1, the number of mol equivalents of compound of formula (II) relative to the number of mol of amino alcohol of formula (V) is between 0.33 (II)/1 (V) and 0.37 (II)/1 (V), the number of equivalents preferably being 0.35 (II)/1 (V).

In another advantageous embodiment of the process of the invention described by scheme S-1, the number of mol equivalents of compound of formula (II) relative to the number of mol of compound of formula (III) is between 0.33 and 0.37 equivalent of (II), preferably 0.35 equivalent of (II).

More specifically, the process of the invention according to scheme S-1 comprises the reaction, in toluene, of trimethylboroxine of formula (IIA) with trimethyl orthoformate of formula (IIIA) in the presence of methanesulfonic acid, and the addition of (R)- or (S)-2-(diphenylhydroxymethyl)pyrrolidine of formula (V) according to scheme S-1A.

The reaction is carried out at a temperature of 20° C.

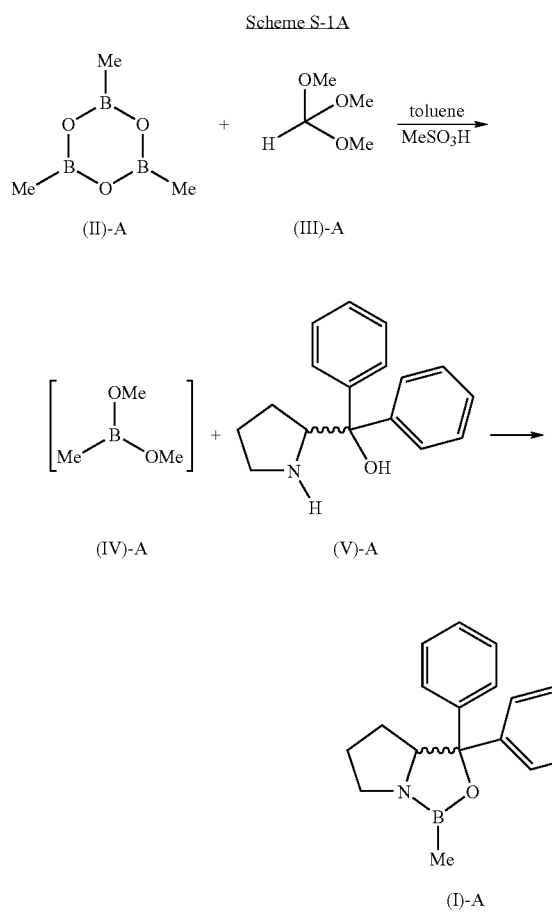

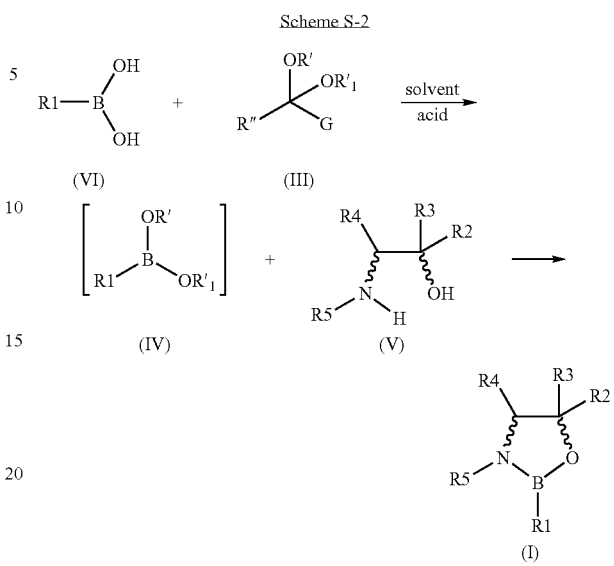

In one advantageous embodiment of the process of the invention described by scheme S-2, the compound of formula (VI) used is an alkylboronic or arylboronic acid. Commercially available products which may be mentioned as examples, but without implying a limitation, are methylboronic acid, phenylboronic acid and p-tolylboronic acid.

In one advantageous embodiment of the process of the invention described by scheme S-2, the compounds of formulae (III) and (V) and the acid used are as defined in scheme S-1.

In one advantageous embodiment of the process of the invention described by scheme S-2, said process is carried out in an organic solvent having the same characteristics as those mentioned in scheme S-1.

The amount of compound of formula (III) used is adjusted to the amount of water present in the solvent.

Preferably, the solvent used is toluene.

In one advantageous embodiment of the process of the invention described by scheme S-2, said process comprises carrying out the reaction at a temperature of between 5° C. and 30° C., preferably at a temperature of 20° C.

In another advantageous embodiment of the process of the invention described by scheme S-2, the number of mol equivalents of compound of formula (VI) relative to the number of mol of amino alcohol of formula (V) is between 1 and 1.5 equivalents of (VI), preferably 1.2 equivalents of (VI).

In another advantageous embodiment of the process of the invention described by scheme S-2, the number of mol equivalents of compound of formula (III) relative to the number of mol of compound of formula (VI) is between 2 and 2.5 equivalents of (III), preferably 2.1 equivalents of (III).

More specifically, the process of the invention according to scheme S-2 comprises the reaction, in toluene, of methylboronic acid of formula (VIA) with trimethyl orthoformate of formula (IIIA) in the presence of methanesulfonic acid, and the addition of (R)- or (S)-2-(diphenylhydroxymethyl)pyrrolidine of formula (V) according to scheme S-2A.

In a second embodiment, the process of the invention described by scheme S-2 comprises the reaction, in an organic solvent, of a boronic acid of formula (VI) with an acetal of formula (III) in the presence of an acid, and the addition of an amino alcohol of formula (V).

Scheme S-2A

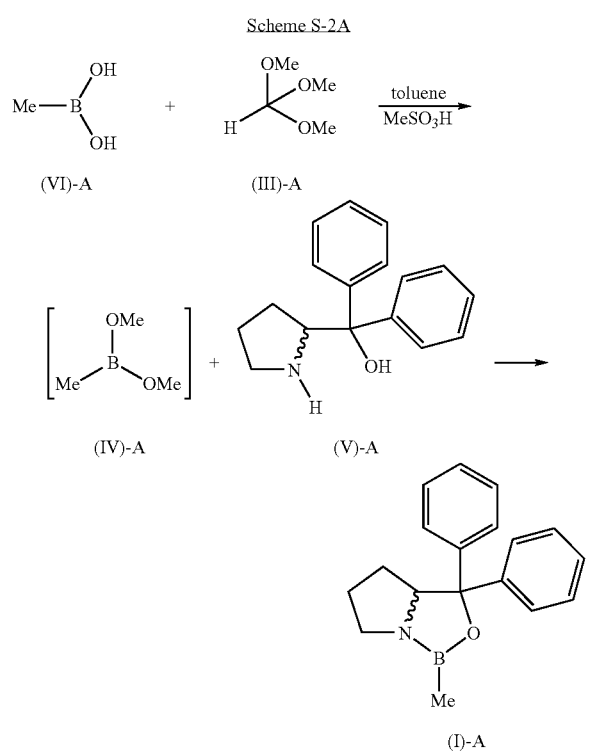

The compound of formula (I) obtained by means of the processes described by schemes S-1 and S-2 is used in a process for the asymmetric reduction of a prochiral ketone, either directly without additional treatment of the medium or after concentration of the medium.

Definitions:

The above definitions are applicable to the description, the Examples and the claims of the invention.

For ease of understanding, the nomenclature of the groups, reactants, solvents or products is the international nomenclature or the nomenclature commonly used by those skilled in the art.

The term "alkyl" denotes a linear or branched C1-C6 hydrocarbon chain. Methyl, ethyl and tert-butyl are mentioned as examples.

The term "aryl" denotes a substituted or unsubstituted C6-C12 aromatic ring. Phenyl and naphthyl are mentioned as examples.

The term "substituent" denotes a halogen atom X', an alkyl (Alk), an aryl (Ar), a hydroxyl (—OH), an alkoxy (—OAlk), an aryloxy (—OAr), an alkyl or aryl ester (—COOAlk or —COOAr), an amino ((—NH$_2$), (—NHR6), (—NR6R7)), an amidine (—C(=NR6)NR6R7, —S(=NR6)NR6R7, —PR8 (=NR6)NR6R7)), an imino (—C(=NR6)R7), a cyano (—CN), a nitro (—NO$_2$), a sulfhydryl (—SH), a thioether (—SR9), a sulfate (—OS(O)$_2$OR6), a sulfonate (—S(O)$_2$OR6), a sulfamoyl (—S(O)$_2$NR6R7), a sulfonyl (—SO$_2$R6), a cycloalkyl or a heteroaryl, where R6, R7 or R8 is an alkyl or an aryl.

By way of example, but without implying a limitation, the organic acid can be a sulfonic acid (methanesulfonic acid, paratoluenesulfonic acid).

By way of example, but without implying a limitation, the Lewis acid can be a boron trihalide, an aluminum trihalide or an iron trihalide.

By way of example, but without implying a limitation, the mineral acid can be hydrochloric acid, hydrobromic acid or sulfuric acid.

By way of example, but without implying a limitation, the organic solvent can be a sulfoxide such as dimethyl sulfoxide (DMSO), a nitrile such as acetonitrile, an alcohol such as ethanol, tert-butanol or isopropanol (IPA), a halogenated solvent such as dichloromethane (CH$_2$Cl$_2$), an amide such as dimethylformamide (DMF), an ether such as ethyl ether, a hydrocarbon such as hexane, an aromatic solvent such as toluene, an ester such as ethyl acetate, etc.

Other objects, characteristics and advantages of the invention will become clearly apparent from the following explanatory description including several Examples of the invention, which are given simply by way of illustration and cannot in any way limit the scope of the invention.

In the Examples the percentages are given by weight, the temperature is room temperature (22° C.±3° C.) or is given in degrees Celsius, and the pressure is atmospheric pressure, unless indicated otherwise.

Furthermore, each Example forms an integral part of the invention and any characteristic that appears novel relative to any STATE OF THE ART forms an integral part of the invention and is claimed as such in its generality as a general means, and in its function.

EXAMPLES OF THE INVENTION

Preparation of the Compound (R)-MeCBS

Example 1

Process According to Scheme S-1

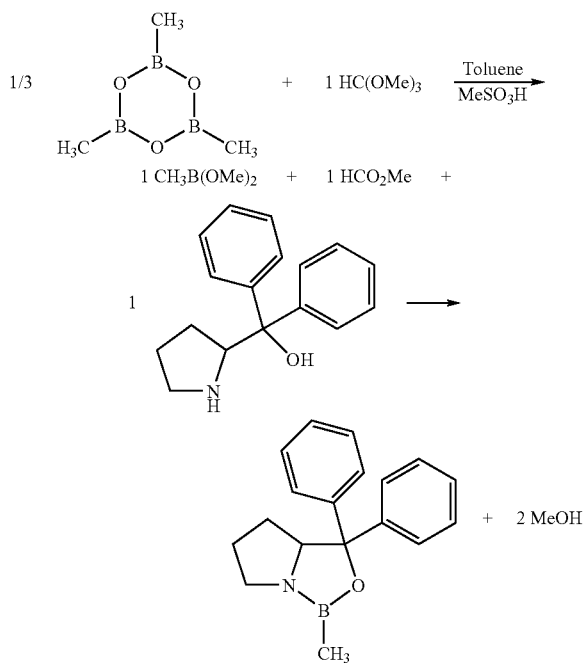

| Compound | Amount | Number of mol | Equivalence |
|---|---|---|---|
| (R)-diphenylprolinol | 5 g | 0.0197 | |
| Trimethylboroxine | 961.4 µl<br>867.2 mg (crude)<br>867.2 mg (pure) | $6.9 \cdot 10^{-3}$ | 0.35 eq. |
| Trimethyl orthoformate | 2.37 ml<br>2.3 g | 0.0217 | 1.1 eq. |
| Toluene | 25 ml | | 5 vol. |
| Methanesulfonic acid | 12.9 µl<br>19.1 mg (crude)<br>19 mg (pure) | $2 \cdot 10^{-4}$ | $1 \cdot 10^{-2}$ eq. |

5 ml of toluene and then 960 µl of trimethylboroxine and 2.4 ml of trimethyl orthoformate are introduced into a four-necked flask under a nitrogen atmosphere. 13 µl of methanesulfonic acid are added to the solution.

An 11° C. exotherm is observed.

The medium is cooled to room temperature. A solution of 5 g of (R)-diphenylprolinol in 18 ml of toluene is added to the above medium.

A 2° C. exotherm is observed.

The medium is stirred at room temperature for 1 hour.

10 ml of toluene are distilled under atmospheric pressure and 10 ml of anhydrous toluene are then added. The medium is concentrated until a 15 to 20% by weight solution of (R)-MeCBS in toluene is obtained.

Example 2

Process According to Scheme S-2

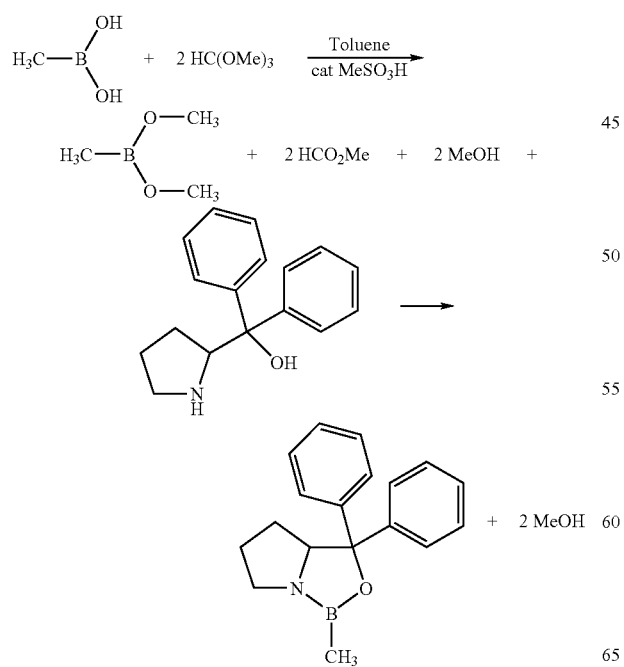

| Compound | Amount | Number of mol | Equivalence |
|---|---|---|---|
| (R)-diphenylprolinol ((R)-DPP) | 4.2 g | 0.0166 | |
| Methylboronic acid | 1.02 g (crude)<br>0.992 g (pure) | 0.0166 | 1 eq. |
| Trimethyl orthoformate | 3.81 ml<br>3.69 g | 0.0348 | 2.1 eq. |
| Toluene | 21 ml | | 5 vol. |
| Methanesulfonic acid | 10.8 µl<br>16 mg (crude)<br>15.9 mg (pure) | $1.66 \cdot 10^{-4}$ | $1 \cdot 10^{-2}$ eq. |

0.99 g of methylboronic acid, 5 ml of toluene and 11 µl of methanesulfonic acid are placed in a four-necked flask under a nitrogen atmosphere. 3.8 ml of trimethyl orthoformate are added to the suspension at room temperature to give a clear solution. The funnel is rinsed with 5 ml of toluene.

A solution of 4.2 g of (R)-diphenylprolinol in 10 ml of toluene is added to the above medium at room temperature.

The funnel is rinsed with 1 ml of toluene. 10 ml of anhydrous toluene are added. The mixture is stirred for 1 hour at room temperature.

25 ml of solvent are distilled under atmospheric pressure to give a 45% by weight solution of (R)-MeCBS in toluene.

Use of the solution of the compound of formula (I) in a reaction for the asymmetric reduction of a prochiral ketone Example 3

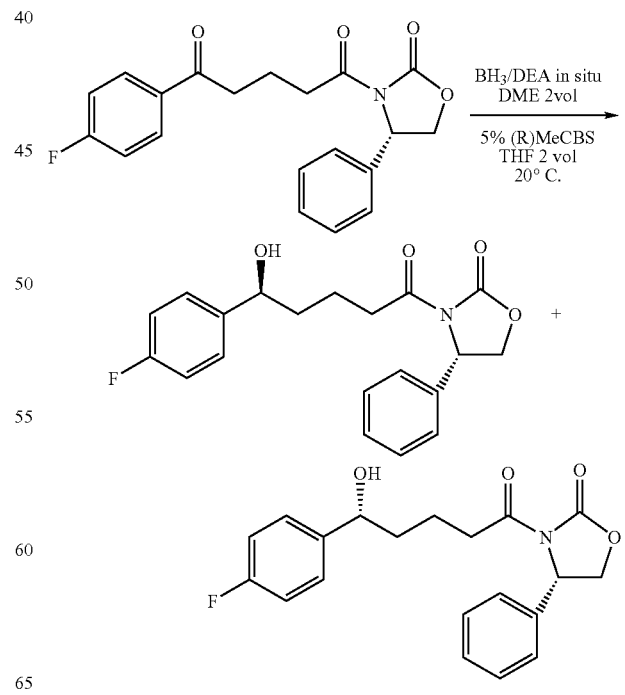

| Compound | Amount | Number of mol | Equivalence |
|---|---|---|---|
| Ketone | 5 g | 0.0141 | |
| (R)-diphenylprolinol methyloxazaboroline ((R)-Me-CBS) | 178 mg | 7.03 · 10⁻⁴ | 5 · 10⁻² eq. |
| Water | 30 ml | | 6 vol. |
| Toluene | 1 ml | | 0.2 vol. |
| Tetrahydrofuran (THF) | 10 ml | | 2 vol. |
| Potassium carbonate (K₂CO₃) | 2.53 g | 0.0183 | 1.3 eq. |
| Acetone: 3 equivalents/BH₃ | 3 ml 2.4 g | | 0.61 vol. |
| Borane-N,N-diethylaniline (BH₃-DEA) | 2.5 ml 2.29 g | 0.0141 | 1 eq. |

7.5 ml of tetrahydrofuran (THF) and 2.5 ml of borane-N,N-diethylaniline complex (BH₃-DEA) are introduced into a four-necked flask under a nitrogen atmosphere. The funnel is rinsed with 2.5 ml of THF. 0.6 ml (178 mg) of the 45% by weight solution of (R)-MeCBS in toluene obtained in Example 2 is added to the medium.

The medium is stirred for 30 min at room temperature. A solution of 5 g of ketone in 10 ml of THF is added over 1 hour at a temperature of 18-20° C. 3 ml of acetone are then added and the medium is stirred for 15 min.

2.5 g of potassium carbonate are dissolved in 30 ml of water. The reaction medium is poured into the potassium carbonate solution. The medium is stirred for 30 min at a temperature of between 20 and 30° C. 30 ml of toluene are added, the mixture is decanted and the phases are separated.

The aqueous phase is re-extracted with 20 ml of toluene.

The organic phases are pooled and then washed twice with 20 ml of water.

The reaction is analyzed by chiral HPLC. The diastereoisomeric excess is 98.1%.

What is claimed is:

1. A process for the preparation of the compounds of formula (I):

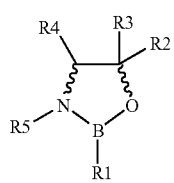

in which:
R1 is an alkyl or an aryl;
R2, R3, R4 and R5 independently are a hydrogen atom, an alkyl or an aryl, it being possible for the alkyl or aryl groups to have one or more hydrogen atoms replaced by one or more substituents;
R4 and R5 together form a heterocycle with the nitrogen atom, which itself comprises one or more substituents; and
R4 and R3 together form a carbocycle, which itself comprises one or more substituents, wherein the process comprises reacting, in two steps:
a) a boric precursor compound selected from the group consisting of:

i) a boroxine of formula (II):

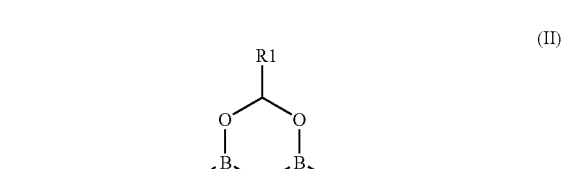

; and of
ii) a boronic acid of formula (VI):

with a compound of formula (III)

to give a boronate compound of formula (IV):

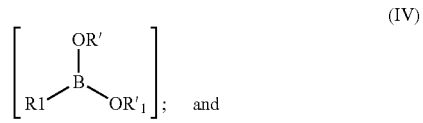

b) the boronate compound of formula (IV) with an amino alcohol compound of formula (V):

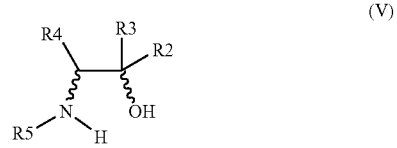

wherein:
G is an alkoxy group (OR'2) or an amino group (NR'R'1);
R', R'1, and R'2 are identical or different and are an alkyl group or an acyl;
R' and R'1 can together form a 5 or 6 membered heterocycle optionally substituted by an alkyl;
R" is a hydrogen atom, an alkyl group or an aryl group; and
R1, R2, R3, R4 and R5 are as defined above,
to give the above-mentioned compound of formula (I).

2. The process of claim 1, wherein the compound of formula (II) is a trialkylboroxine or a triarylboroxine.

3. The process of claim 1, wherein the compound of formula (II) is trimethylboroxine.

4. The process of claim 1, wherein the compound of formula (III) is selected from the group comprising a trialkyl or triaryl orthoformate, a formamide acetal and a trimethoxymethylaryl and trimethoxymethylalkyl compound.

5. The process of claim 1, wherein the compound of formula (III) is selected from the group consisting of trimethyl orthoformate trimethoxymethane, dimethylformamide dimethylacetal, trimethoxymethylbenzene, 1,1,1-trimethoxyethane, 1,1,1-trimethoxypropane and 1,1,1-trimethoxy-2-methylpropane.

6. The process of claim 1, wherein the reaction takes place in the presence of an acid selected from an organic acid, a Lewis acid and a mineral acid.

7. The process of claim 6, wherein the acid used is methanesulfonic acid (MeSO$_3$H).

8. The process of claim 1, wherein the reaction takes place in at least one organic solvent, used by itself or in a mixture, which is selected from an alcohol, a halogen compound, an aromatic compound, a nitrile compound, an ether compound and an ester compound.

9. The process of claim 8, wherein the reaction takes place in the organic solvent, used by itself or in a mixture, and the amount of the compound of formula (III) is adjusted to the amount of water present in the solvent used; and wherein the compound of formula (III) is present in an excess molar amount relative to the boric precursor compound so as to absorb the amount of water present in the solvent used and the water formed in the medium.

10. The process of claim 1, wherein the reaction takes place in an organic solvent consisting of toluene.

11. The process of claim 1, wherein the compound of formula (VI) is an alkylboronic or arylboronic acid.

12. The process of claim 1, wherein the compound of formula (VI) is methylboronic acid.

13. The process of claim 1, wherein the amino alcohol of formula (V) is a supported or unsupported, optically active compound.

14. The process of claim 1, wherein the amino alcohol of formula (V) is selected from the group consisting of:
(R)- or (S)-2-(diphenylhydroxymethyl)pyrrolidine;
(R)- or (S)-2-(2-dinaphthylhydroxymethyl)pyrrolidine;
(1R,2S)-1-amino-2-indanol, (R)- or (S)-2-amino-3-methyl-1,1-diphenyl-1-butanol;
(R)- or (S)-2-amino-3,3-dimethyl-1,1-diphenyl-1-butanol;
(R)- or (S)-2-hydroxymethylindoline;
(R)- or (S)-α,α-diphenyl(indolin-2-yl)methanol;
(R)- or (S)-(5,5-dimethylthiazolidin-4-yl)diphenylmethanol; and
2-((1R,2R,3R,5S)-2-amino-6,6-dimethylbicyclo[3.1.1]hept-3-yl)ethanol or another optically active isomer.

15. The process of claim 1, wherein the amino alcohol of formula (V) is (R)- or (S)-2-(diphenylhydroxymethyl)pyrrolidine.

16. The process of claim 1, wherein the number of mol equivalents of compound of formula (II) relative to the number of mol of amino alcohol of formula (V) is ranging between 0.33 (II)/1 (V) and 0.37 (II)/1 (V).

17. The process of claim 1, wherein the number of mol equivalents of compound of formula (VI) relative to the number of mol of amino alcohol of formula (V) is between 1 and 1.2 equivalents of (VI).

18. The process of claim 1 wherein a compound of formula IA, named Alkyl-CBS, is prepared:

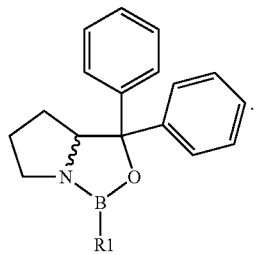

(IA)

19. A process for the asymmetric reduction of a prochiral ketone, comprising:

a) preparing, in a reaction medium, a compound of formula (I):

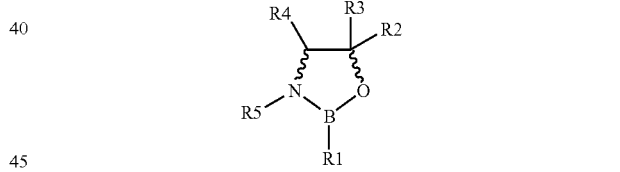

(I)

by the process as defined in claim 1; and b) performing an asymmetric reduction of a prochiral ketone in the presence of said compound of formula (I).

20. The process of claim 19, wherein the asymmetric reduction is performed with use of the compound of formula (I) either without additional treatment of the reaction medium, or after concentration of the medium.

21. The process of claim 19, wherein the asymmetric reduction is performed in a solvent comprising or consisting essentially of tetrahydrofuran, THF.

22. The process of claim 19, wherein the asymmetric reduction is performed in the presence of a complex boran-N,N-diethylaniline, named BH3-DEA.

23. The process of claim 19, wherein the asymmetric reduction is performed with a compound Alkyl-CBS of formula (IA):
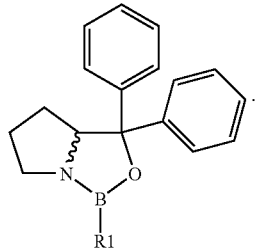
(IA)
24. The process of claim 19, wherein the ketone is:
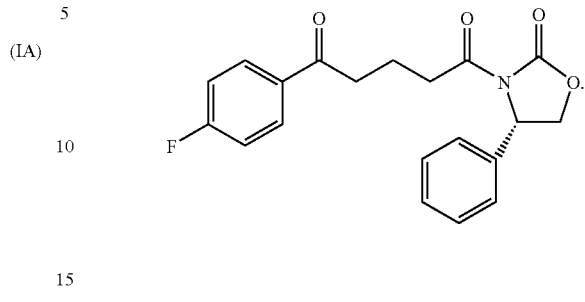
* * * * *